US012195788B2

(12) United States Patent
Koculi et al.

(10) Patent No.: US 12,195,788 B2
(45) Date of Patent: Jan. 14, 2025

(54) HIGH-THROUGHPUT AND SINGLE NUCLEOTIDE RESOLUTION TECHNIQUES FOR THE DETERMINATION OF RNA POST-TRANSCRIPTIONAL MODIFICATIONS

(71) Applicant: UNIVERSITY OF CENTRAL FLORIDA RESEARCH FOUNDATION, INC., Orlando, FL (US)

(72) Inventors: Eda Koculi, Oviedo, FL (US); Riley Gentry, Lawrence, KS (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 362 days.

(21) Appl. No.: 16/477,764

(22) PCT Filed: Jan. 12, 2018

(86) PCT No.: PCT/US2018/013577
§ 371 (c)(1),
(2) Date: Jul. 12, 2019

(87) PCT Pub. No.: WO2018/132712
PCT Pub. Date: Jul. 19, 2018

(65) Prior Publication Data
US 2019/0382832 A1 Dec. 19, 2019

Related U.S. Application Data

(60) Provisional application No. 62/445,376, filed on Jan. 12, 2017.

(51) Int. Cl.
*C12Q 1/68* (2018.01)
*C12Q 1/6827* (2018.01)
*C12Q 1/6869* (2018.01)

(52) U.S. Cl.
CPC ......... *C12Q 1/6827* (2013.01); *C12Q 1/6869* (2013.01); *C12Q 2521/107* (2013.01); *C12Q 2527/127* (2013.01); *C12Q 2527/137* (2013.01); *C12Q 2535/122* (2013.01); *C12Q 2537/164* (2013.01)

(58) Field of Classification Search
CPC ............... C12Q 1/6827; C12Q 1/6869; C12Q 2521/107; C12Q 2527/127; C12Q 2527/137; C12Q 2535/122; C12Q 2537/164
See application file for complete search history.

(56) References Cited

U.S. PATENT DOCUMENTS

2014/0030808 A1* 1/2014 Sahin ................. A61P 43/00
435/377

FOREIGN PATENT DOCUMENTS

WO WO-2015054247 A1 * 4/2015 ............. C12N 15/01

OTHER PUBLICATIONS

Achuthan et al (BMC Biochemistry, 2015; 16, 12, p. 2-14) (Year: 2015).*
Imashimizu et al. (Nucleic Acids Research 2013, 41(19):9090-9104) (Year: 2013).*
Hauenschild et al. (Nucleic Acids Research, 2015, 9950-9964) (Year: 2015).*
PCT search report & written opinion, PCT/US2018/013577, mailed May 9, 2018, 14 pages.
Achuthan, Vasudevan et al., "Alternative divalent cations (Zn2+, Co2+, and Mn2+) are not mutagenic at conditions optimal for HIV-1 reverse transcriptase activity", BCM Biochemistry, 2015, vol. 16, No. 2, 14 pages.
Bodi, Zsuzsanna et al., "Yeast targets for mRNA methylation", Nucleic Acids Research, 2010, vol. 38, No. 16, pp. 5327-5335.
Desrosiers, Ronald et al., "Identification of Methylated Nucleosides in Messenger RNA from Novikoff Hepatoma Cells", Proc. Nat. Acad. Sci., Oct. 1974, vol. 71, No. 10, pp. 3971-3975.
Dominissini, Dan et al., "Topology of the human and mouse m6A RNA methylomes revealed by m6A-seq", Nature, May 10, 2012, vol. 485, 8 pages.
Findeiß, Sven et al., "Traces of Post-Transcriptional RNA Modifications in Deep Sequencing Data", Jan. 12, 2011, 10 pages.
Gentry, Riley C. et al., "Time course of large ribosomal subunit assembly in E. coli cells overexpressing a helicase inactive DbpA protein", RNA, 2016, vol. 22, pp. 1055-1064.
Hauenschild, Ralf et al., "The Reverse Transcription Signature of N-1-Methyladenosine in RNA-Seq is Sequence Dependent", Nucleic Acids Research, No. 2015, vol. 43, No. 20, pp. 9950-9964.
Iida, Kei et al., "Bioinformatics analysis suggests base modifications of tRNAs and miRNAs in Arabidopsis thaliana", BMC Genomics 2009, vol. 10, No. 155, 11 pages.
Lichinchi, Gianluigi et al., "Dynamics of Human and Viral RNA Methylation during Zika Virus Infection", Cell Host & Microbe, 2016, vol. 20, pp. 666-673.
Liu, Nian et al., "Probing N6-methyladenosine RNA modification status at single nucleotide resolution in mRNA and long noncoding RNA", RNA, 2013, vol. 19, pp. 1848-1856.

(Continued)

*Primary Examiner* — Stephanie K Mummert
(74) *Attorney, Agent, or Firm* — Timothy H. Van Dyke; WOLTER VAN DYKE DAVIS, PLLC

(57) ABSTRACT

Disclosed herein are methods and associated compositions and kits for identifying nucleoside modifications. Particularly exemplified herein are methods that involve inducing base misincorporation at locations in an RNA that harbor a nucleoside modification. The resulting cDNA can then be subjected to next generation sequencing to identify mutations with respect to a reference sequence. Moreover, the type of nucleoside modification can be determined based on the substitution pattern of a given nucleoside modification.

11 Claims, No Drawings

(56) References Cited

OTHER PUBLICATIONS

Lovejoy, Alexander F. et al., "Transcriptome-Wide Mapping of Pseudouridines: Pseudouridine Synthases Modify Specific mRNAs in S. cerevisiae", Plos One, 2014, vol. 9, No. 10, 15 pages.

Maden, B. edward H., "Mapping 28-O-Methyl Groups in Ribosomal RNA", Methods, 2001, vol. 25, pp. 374-382.

McGuinness DH et al., "m6a RNA Methylation: The Implications for Health and Disease", Journal of Cancer Science and Clinical Oncology, 2014, vol. 1, issue 1, 7 pages.

Ordonez, Heather et al., "Mycobacterium smegmatis DinB2 misincorporates deoxyribonucleotides and ribonucleotides during templated synthesis and lesion bypass", Nucleic Acids Research, 2014, vol. 42, No. 20, pp. 12722-12734.

Seidel, A. et al., "Modified nucleosides: an accurate tumour marker for clinical diagnosis of cancer, early detection and therapy control", British Journal of Cancer, (2006) vol. 94, pp. 1726-1733.

Shajani, Zahra et al., "Assembly of Bacterial Ribosomes", Annu. Rev. Biochem., 2011, vol. 80, pp. 501-526.

Siegfried, Nathan A. et al., "RNA motif discovery by Shape and mutational profiling (Shape-MaP)", Nature Methods, Sep. 2014, vol. 11, No. 9, pp. 14 pages.

Sloan, Katherine E. et al., "Tuning the ribosome: The influence of rRNA modification on eukaryotic ribosome biogenesis and function", RNA Biology, 2017, vol. 14, No. 9, pp. 1138-1152.

Smola, Matthew J. et al., "Selective 2'-hydroxyl acylation analyzed by primer extension and mutational profiling (Shape-MaP) for direct, versatile and accurate RNA structure analysis", Nature Protocols, 2015, vol. 10, No. 11, pp. 1643-1669.

Tang, Chong et al., "ALKBH5-dependent m6A demethylation controls splicing and stability of long 3'-UTR mRNAs in male germ cells", PNAS, Dec. 26, 2017, E325-E333.

Tavares, Rafael de Cesaris Araujo et al., "MRT-ModSeq—Rapid detection of RNA modifications with MarathonRT", bioRxiv preprint doi: https://doi.org/10.1101/2023.05.25.542276, May 25, 2023, 45 pages.

Tijerina, Pilar et al., "DMS footprinting of structured RNAs and RNA-protein complexes", Nature Protocols, 2007, vol. 2, No. 10, pp. 2608-2623.

Willyard, Cassandra, "A new twist on epigenetics", Nature, Feb. 23, 2017, vol. 542, pp. 406-408.

Wu, Jinjun et al., "N6-Hydroperoxymethyladenosine: a new intermediate of chemical oxidation of N6-methyladenosine mediated by bicarbonateactivated hydrogen peroxide", Chem. Sci., 2015, vol. 6, pp. 3013-3017.

Zheng, Guanqun et al., "Sprouts of RNA epigenetics", Biology, Jun. 2013, vol. 10, No. 6, pp. 915-918.

Lai, Ming-Derg et al., "Influence of divalent metal activator on the specificity of misincorporation during DNA synthesis catalyzed by DNA polymerase I of *Escherichia coli* ", Mutation Research, 198 (1988) 27-36.

\* cited by examiner

HIGH-THROUGHPUT AND SINGLE NUCLEOTIDE RESOLUTION TECHNIQUES FOR THE DETERMINATION OF RNA POST-TRANSCRIPTIONAL MODIFICATIONS

STATEMENT REGARDING FEDERALLY SPONSORED RESEARCH

This invention was made with Government Support under Grant No. R21CA175625 awarded by the National Institutes of Health and Grant No. 1649522 awarded by the National Science Foundation. The Government has certain rights to the invention.

BACKGROUND

At the moment methods for the detection of the RNA postranscriptional modifications at the single nucleotide level and high throughput are largely missing[1, 3]. RNA post-transcriptional modifications have been implicated in various cancer cell propagation such as leukemia, colorectal, endometrial, stomach, prostate and breast cancers, and they have shown to play a role in Parkinson's diseases, attention deficit disorder, addiction, epilepsy, bacterial and viral infections, including Zika[1, 3, 4]. The lack of effective techniques for the determination of the RNA post-transcriptional modification makes it challenging: (i) to investigate the function of these modifications on human disease[1], (ii) to develop novel methods for numerous diseases detection, (iii) to design and develop drugs that target the RNA post-transcriptional modifications. Presently, most techniques used for the determination of the RNA post-transcriptional modifications: (i) require the RNA molecule purification before determining its post-transcriptional modifications[5-7], (ii) are intricate and time consuming[5, 7, 8], (iii) have difficulty identifying the exact modified base in an RNA sequence[6, 8]. Thus, novel techniques for the determination of RNA post-transcriptional modification are of great public health, biotech and pharmaceutical industry interests.

DETAILED DESCRIPTION

Disclosed herein are methods and associated compositions and kits for identifying nucleoside modifications. Methods have been developed that involve inducing base misincorporation at locations in an RNA that harbor a nucleoside modification. This misincorporation is dictated by certain constituents provided in the reverse transcription reaction mix, namely including an amount of $Mn^{2+}$. The resulting cDNA can then be subjected to next generation sequencing to identify mutations with respect to a reference sequence. Moreover, the type of nucleoside modification can be determined based on the substitution pattern of a given nucleoside modification. For example, if interrogation of an RNA molecule reveals a nucleoside modification at a given locus, the type of nucleoside modification can be elucidated by comparing to previously determined substitution patterns for a given modification (see e.g. Table 1 infra). Embodiments described herein are able to identify at single nucleotide resolution 10 out of 100 known post-transcriptional RNA modifications[1, 2].

Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention generally are performed according to conventional methods well known in the art and as described in various general and more specific references, unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et ah, Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The term "next generation sequencing" or "NGS" as used herein refers to sequencing techniques that elucidate a nucleic acid sequence by analyzing numerous fragments of that nucleic acid sequence in parallel. Examples of next generation sequencing include (i) sequencing by synthesis of single-molecule arrays with reversible terminators (e.g. Illumina/Solex approach, see S. Bennett, Solexa Ltd, *Pharmacogenomics* 5 (2004) 433-438; S. T. Bennett, C. Barnes, A. Cox, L. Davies, C. Brown, Toward the 1,000 dollars human genome, *Pharmacogenomics* 6 (2005) 373-382; and The term "RNA containing sample" as used herein refers to a sample that contains RNA to be analyzed. D. R. Bentley, Whole-genome re-sequencing, *Curr. Opin. Genet. Dev.* 16 (2006) 545-552)); (ii) pyrosequencing in high-sensity picoliter reactors (e.g. 454/Roche FLX system technology, M. Margulies, et al., Genome sequencing in microfabricated high-density picolitre reactors, *Nature* 437 (2005) 376-380); and (iii) massively parallel sequencing by ligation (e.g. ABI/SOLiD approach; J. Shendure, et al., Accurate multiplex polony sequencing of an evolved bacterial genome, *Science* 309 (2005) 1728-1732).

The term "modified nucleoside" as used herein refers to the nucleosides adenosine, inosine, cytidine, uridine, guanosine, or 7-deazaguanosine that have been modified from their canonical form. Examples of modifications to nucleosides include Pseudouridylation, 2'-O-methylation, and base methylation. Provided below are specific nucleoside modifications that can be identified by the method embodiments disclosed herein.

The term "presence of $Mn^{2+}$" as used herein refers to an amount of $Mn^{2+}$ used in a reverse transcription reaction sufficient to generate misincorporation of a nucleoside at a locus in an RNA having a nucleoside modification. In specific embodiments, the amount of $Mn^{2+}$ comprises 0.01 mM to 40 mM in the reverse transcription reaction mixture. In a more specific embodiment, the amount of $Mn^{2+}$ comprises 1-10 mM.

Methods

According to one embodiment, disclosed is a method for detecting an RNA post-transcriptional modification in a sample. The method involves performing a reverse transcription reaction of an RNA in the presence of $Mn^{2+}$ to generate cDNA, wherein the Mn2+ is at a concentration sufficient to induce a base misincorporation at a location of the RNA comprising a nucleoside modification; and performing next generation sequencing on the cDNA under conditions to detect the base misincorporation.

In a specific method embodiment, the nucleoside modification detected includes of m2G (N2-methylguanosine), m3Ψ (3-methylpseudouridine), 5-hydroxylC (5-hydroxyl cytosine), m7G (7-methylguanosine), m4Cm (N4,2'-O-dimethylcytosine), m3U (3-methyluridine), m6,6 A (N6, N6-dimethyladenosine), m1G (1-methylguanosine), m6 A (N6-methyladenosine), m5U (5-methyluridine), Cm (2'-O-methylcytidine), Um (2'-O-methyluridine), Am (2'O-methyladenosine), Gm (2'-O-methylguanosine), Ψ (pseudouridine), m1A (1-methyladenosine), or a combination thereof.

In an even more specific embodiment, the nucleoside detected includes m2G (N2-methylguanosine), m3Ψ (3-methylpseudouridine), 5-hydroxylC (5-hydroxyl cytosine), m7G (7-methylguanosine), m4Cm (N4,2'-O-dimethylcytosine), m3U (3-methyluridine), m6,6 A (N6, N6-dimethyladenosine), m1G (1-methylguanosine), or a combination thereof. Further still, the nucleoside modification includes m6 A (N6-methyladenosine), m5U (5-methyluridine), Cm (2'-O-methylcytidine), Um (2'-O-methyluridine), Am (2'O-methyladenosine), Gm (2'-O-methylguanosine), Ψ (pseudouridine), m1A (1-methyladenosine), or a combination thereof.

In a specific embodiment, performing the next generation sequencing involves converting the cDNA fragments into dsDNA; fragmenting the dsDNA; and performing sequencing on the dsDNA fragments that employs pyrosequencing, sequencing by ligation or sequencing by synthesis methodologies.

In alternative embodiments, a method for detecting an RNA post-transcriptional modification in a sample involves obtaining a sample that has been prepared by already performing one or more steps in the broader method. For example, the method may involve identifying one or more mutations in a DNA nucleic acid sequence in obtained sample made as a result of subjecting a RNA to reverse transcriptase in the presence of Mn2+; wherein a locus of a mutation of the one or more mutations represents a nucleoside modification. The sample may pertain to a dsDNA library of fragments to which next generation sequencing is performed. Performing next generation sequencing on the dsDNA library of fragments may involve obtaining sequence data via pyrosequencing, sequencing by ligation or sequencing by synthesis methodologies; and aligning the sequence data to generate aligned sequence data. The aligned sequence data is then compared to a reference sequence and mutation frequencies are calculated in the aligned sequence data. In a specific embodiment, the nucleoside modification type of the nucleoside modification is determined based on a substitution pattern of the corresponding mutation.

In an alternative embodiment, a method is disclosed that involves obtaining aligned sequence data of a RNA that has been subjected to reverse transcription in the presence of Mn2+ and next generation sequencing; identifying one or more mutations in the aligned sequence data relative to a reference sequence; and determining one of the following based on the identifying step:

(i) a cell type in which the RNA was produced;
(ii) whether a cell type in which the RNA was produced is cancerous; and (iii) whether the biological source of the sample is a twin of another sample.

Compositions

Based on the discoveries provided herein, new compositions have been developed that are particularly tailored for implementation with method embodiments disclosed herein. In one example, a reverse transcriptase buffer composition is provided that includes a Tris compound; a potassium salt; a reducing agent; and a manganese salt. Examples of a Tris compound include Tris acetate or Tris hydrochloride. Examples of the manganese salt include manganese chloride or manganese acetate. An example of a reducing agent is dithiothreitol. Examples of the potassium salt include potassium chloride or potassium acetate. The reverse transcription buffer composition may alternatively include deoxynucleotide triphosphates (dNTPs). The level of individual dNTPs (e.g. A, G, C and U) may be altered to optimize the reverse transcription reaction depending on the type or brand of reverse transcriptase used.

Kits

Further, based on the discoveries disclosed herein, kits are provided which contain components specifically tailored to assist in induction of nucleoside misincorporation. In one embodiment, a reverse transcription kit is provided that includes an amount of an reverse transcription buffer composition that includes a manganese salt; and one or more of the following:

(i) an amount of an RT primer containing composition;
(ii) an amount of a dNTP containing composition; and (ii an amount of a reverse transcriptase containing composition.

Screening

The methods and discoveries disclosed herein also enable screening for agents that induce or inhibit nucleoside modifications (nucleoside modification modulator or NMM agent). For example, a screening method may involve subjecting a cell to a test agent; obtaining an RNA sample from the test agent; and determining whether the RNA sample comprises one or more nucleoside modifications by performing reverse transcription on the RNA sample in the presence of $Mn^{2+}$ to produce a cDNA, performing next generation sequencing of the cDNA to produced aligned sequence data and identifying one or more mutations in the aligned sequence data relative to a reference sequence. The presence or absence of nucleoside modifications identified in the RNA sample can be compared to a control RNA sample, A control RNA sample is typically a corresponding RNA from same cell type but where the cell has not been subjected to the test agent. The test agent may be identified as an NMM if a number or type of nucleoside modifications in the RNA sample differs from the control RNA sample.

EXAMPLES

Example 1: Identification of Post-Transcriptional Modifications in 5S, 16S and 23S Ribosomal RNA Subunits from *Escherichia Coli*

Results

The 30S and 50S subunit from *Escherichia Coli* (*E. coli*) were isolated using the sucrose gradient technique and purified the 5S, 16S and 23S ribosomal RNA via phenol extraction and ethanol precipiation[9]. Next, reverse transcriptase reaction was performed on the 5S, 16S and 23S ribosomal RNA in the presence of $Mn^{2+}$ and SuperScript II enzyme. The reverse transcriptase reaction was performed with six nucleotide long random primers; however, the reverse transcriptase reaction could also be performed with primer specific for an RNA molecule. In that case, the RNA molecule does not need to be separated from other RNA molecules. Subsequently, next generation sequencing (NGS) was performed to determine the sequence of cDNA product.

The analysis of the next generation sequencing data of the reverse transcriptase product shows base misincorporation at a number of previously known ribosomal RNA base modifications (Table 1). These modifications are: m2G (N2-methylguanosine), m3Ψ (3-methylpseudouridine), m4Cm (N4,2'-O-dimethylcytosine), m3U (3-methyluridine), m6,6 A (N6, N6-dimethyladenosine), m1G (1-methylguanosine).

Treatment of RNA samples with N-cyclohexyl-N-β(4-methylmorpholinium) ethylcarbodiimide p-tosylate (CMCT)[10] produces adduct with G bases at position N1, U bases at position N3, and bases at positions N3 and N1[10, 11]. Treatment of the reaction mixture with $NaHCO_3$ (final pH 10.4) hydrolyzes all adducts formed between CMCT and the RNA bases with the exception of adducts formed between CMCT and N3 of Ψ[10, 11]. This adduct produces the termination of the reverse transcriptase reaction preformed in presence of $Mg^{2+}$ at precisely one base before Ψ[11, 12]. The experimental data provided herein shows that in presence of $Mn^{2+}$, the reverse transcriptase misincorporates a residue at the CMCT modified instead of stopping its polymerase reaction (Table 2, FIG. 1).

Dihydrouridine (D) treatment with CMCT followed by alkaline treatment of reaction at pH 10.4, and reverse transcriptase reaction in presence of $Mn^{2+}$ produces a base misincorporation at the D position (Table 2, FIG. 1). CMCT is not expected to form a stable adduct with D after alkaline treatment[11]. However, previous experiments have shown that treatment of D with alkaline solution produces base opening[13]. Hence, it is very likely the open D ring produces the base misincorporation by reverse transcriptase in presence of $Mn^{2+}$.

Incubation of RNA with CMCT followed by alkaline treatment of the mixture at pH 10.4 also produces misincorporation by reverse transcriptase in present of $Mn^{2+}$ at 7-methylguanosine (m7G) and 5-hydroxycytosine (5-OH C) (Table 3 and 4). CMCT does not stay bound to G or C bases after alkaline treatment[11], hence the misincorporation must be a consequence of alkaline treatment[11]. In fact, alkaline treatment has shown to from an abasic site at m7G position[14]. Moreover, it is very likely that similar to D, alkaline treatment opens the 5-OH C ring.

Cm, Um, Am, Gm have been detected previously by performing the reverse transcriptase in presence of low amount of dNTPs[14-16]. Under this regime and in the presence of $Mg^{2+}$, the reverse transcriptase stops one residue before the modification[15, 16]. It is expected that performing the reaction with 1-100 uM of one dNTP, 1 mM of the other three dNTPs and in presence of SuperScript II plus $Mn^{2+}$ would produce a base misincorporation instead of a stop in the reverse transcriptase reaction at the position of the methylated nucleotide that currently do not produce a base mismatch. The misincorporation will be observed for the base that is at low concentration in the reaction mixture. Examples of modifications that we expect of observe are Cm, Um, Am, Gm and 6 methyl adenosine (m6A).

Dimethyl sulfate treatment of A and C bases produce m1A and m3C. The reverse transcriptase reaction of m1A, m3C bases in presence of $Mn^{2+}$ have shown to produce a mismatch[17, 18]. Hence, our reverse transcriptase reactions in presence of $Mn^{2+}$ are expected to detect the m1A, m3C modifications on RNA. There are no m1A and m3C in *E. coli* ribosome[19], so they were not observed. There are previous studies that involved determination of m1A and m3C as mismatches from the reverse transcriptase reaction performed in presence of $Mn^{2+}$[17, 18], however, that group was looking for artificially induced adducts compared to a control RNA, whereas embodiments herein detect naturally occurring RNA modifications. Both the detection of m2G, m3Ψ, m4Cm, m3U, m6,6 A and m1G and the simultaneous detection of m1A and m3C with those modifications is believed to be reported herein for the first time.

Materials and Methods.

Detection of m1G, m2G, m3Ψ, m4Cm, m3U, and m6,6 A.

First, the 30S and 50S ribosomal particles were isolated using sucrose gradients[9]. Subsequently, the 5S, 16S, 23S was purified from these particles using phenol extraction and ethonol precipitated. RNA form each particles were resuspended in water. Next, 100 ng of RNA was mixed with 200 ng of random six nucleotide long primers, heat at 95° C. for 1 minute, 65° C. for 5 minutes, incubate at 22° C. for 15 minutes and then place on ice. This allows the primers to anneal to RNA. The reaction buffer and 200 unit of SuperScript II enzyme (Thermo Fisher Scientific) were added to the mixture. The reaction buffer consisted of 50 mM Tris pH 8.3, 75 mM KCl, 1 mM each dNTP, 10 mM DTT, 6 mM $MnCl_2$. The reaction mixture was incubated at 22° C. for 10 minutes, at 42° C. for 3 hours and then the SuperScript II enzyme was killed by placing the reaction at 65° C. for 20 minutes. We use the NEB Second strand synthesis kit to convert the cDNA to dsDNA, and then the Illumina Nextera XT kit to add adapters for sequencing. However, the library preparation can be accomplished by a number of methods since the modification sites are encoded into the cDNA as mistakes Following the sequencing reaction (MiSeQ 2×150), the adapter-trimmed reads are aligned using Bowtie 2—although any alignment program which allows for mistakes can be used. The specific alignment parameters used are [This is the ShapeMapper default for bowtie2][20, 21].

'--local', '-D', '20', '-R', '3', '-N', '1', '-L', '15', '-i', 'S,1,0.50', '--score-min', 'G,20,8', '--ma', '2', '--mp', '6,2', '--rdg', '5,1', '--rfg', '5,1', '--dpad', '100', '--maxins', '800', '-p', '4', '-x', Alignment parameters must be adjusted according to the experiment being undertaken. One essential parameter for our adjusted technique is -N 1, which allows for collecting mutations. The alignment is then written into a SAM file and parsed for mutations using the freely available ShapeMapper program[21], which counts deletions and substitutions at each base position relative to the reference sequence, and then computes the mutation frequency [(# Deletions+Substitutions)/number of reads] at each position. Insertions are ignored by the program[21].

The background mutation frequency was calculated by using the mean mutation frequency of the dataset after removing data points corresponding to DNA sequence variations. The DNA sequence variations are a consequence of the fact that E. coli contains 7 copies of ribosomal RNA gene and there are differences on of these genes' sequences.

It was determined that positions with a high frequency of mutations corresponded to RNA bases known from previous experiments to be post-transcriptionally modified[22]. Using the mutation frequencies, all the m2G, m3Ψ, m4Cm, m3U, m6,6 A, m1G modifications in the 16S and 23S ribosomal RNA were determined.

Detection of Ψ, 5-OH C, and D

The RNA was purified as described for the other modifications above. Prior to reverse transcription, 7.5 ug of RNA was incubated with ~250 mM CMCT in a pH 8.4 buffer containing 7M urea and allowed to react at 37 C for 20 minutes. The reaction was stopped by adding an equal volume of 0.5M Acetate pH 5.5, and ethanol precipitated. The precipitate was resuspended in pH 10.4 buffer, and placed at 37 C for 3.5 hours. The reaction was again stopped with 0.5M acetate and precipitated. The precipitate was then resuspended in water and reverse transcribed, prepared into a next generation sequencing library, and sequenced. These reactions were sequenced in parallel with samples which never saw CMCT treatment. The mutations were counted as described for the other modifications in both samples as described above. However, the difference between the mutation rates in the +CMCT and untreated samples were calculated, as well as the fold change (Difference in Mutation Rate at a position divided by the mutation rate of the untreated sample at that position) for every position. Modifications were present at positions where a difference in mutation rate above 2% and a fold change at or above 10-fold were calculated (Tables 2-4).

The chemical treatment of the RNA with CMCT has been previously well characterized, however[11], the use of $Mn^{2+}$ in reverse transcription and counting mutations has not been previously conducted for these modifications: Ψ, 5-OH C, and D.

Discussion

Benefits of the methods provided herein include the following: (i) the RNA molecule does not need to be purified, as the next generation sequencing can be performed and the precise RNA modifications in a mixture of RNA molecules can be achieved by using primers specific to the desired RNA, (ii) identification of a number of post-transcriptional modifications can be carried out simultaneously, (iii) the exact base in the sequence that is modified can be determined; hence, the technique allows single nucleotide resolution detection, (iv) detection of mistakes is advantageous to stops because modified nucleotides near in sequence can be identified by counting mistakes.

The experiments and data herein are the first demonstration of using reverse transcriptase reaction in the presence of $Mn^{2+}$ for the determination of RNA post-transcriptional modifications. Kevin Weeks group aiming to determine RNA secondary and tertiary structure, chemically modified RNA, performed the reverse transcriptase reaction in presence of $Mn^{2+}$ and identified the location of chemically modified bases by comparing via next generation sequencing the misincorporation of bases in chemically modified and unmodified RNA, the control sample[20]. However, the Weeks group disregarded the misincorporations observed in the control chemically untreated RNA sample. They considered these misincorporations experimental noise. The present disclosure represents the first realization that the misincorporations observed in the chemically untreated RNA control sample are a consequence of the post-transcriptional modification process. Hence, present discovery involved detecting the post-transcriptional modifications in what previously was considered noise.

A new computer program was designed which was suggested to work for RNA endogenous post-transcriptional modifications. The specific modifications that the program can detect was not mentioned. The authors of that paper claimed that high background rate of mutations could be a consequence of RNA post-transcriptional modifications[23].

CONCLUSION

High-throughput techniques for the identification of RNA post-transcriptional modifications at single nucleotide resolution while determining the modifications position in the RNA sequence do not exist. Provided herein are methods to identify simultaneously at least nine classes (or at least eighteen classes) of RNA modifications via NGS. More importantly, since the present techniques can detect a methyl group, which is a relatively small group, they can also detect other more bulky RNA modifications. In other words, method embodiments can serve as a platform for the identifications of much larger classes of RNA post-transcriptional modifications.

Our method can detect ring opening in a base, and an abasic site. Future chemical methods that open a specific modified base, or form an abasic site can be used combined with our technique to determine the precisely position and relative extent of modification of a base.

TABLE 1

Modification observed in untreated ribosome sample

| Base[a] | RNA[b] | Modification[c] | Mutation Rate[d] | Substitution Pattern[e] | Fold over background |
|---|---|---|---|---|---|
| G 745 | 23S | m1G | 0.7446 | Del >> T >> A~C | 471 |
| G 1835 | 23S | m2G | 0.6336 | C >> Del > A~T | 401 |
| U 1915 | 23S | m3 Ψ | 0.812 | A >> G >> C~Del | 514 |
| G 2445 | 23S | m2G | 0.048 | C >> T~A~Del | 30 |
| Background | 23S | | 0.00158 | | |
| G 966 | 16S | m2G | 0.02105 | A > T > C~Del | 8 |
| G 1515 | 16S | m2G | 0.04039 | A > T > C~Del | 16 |
| G 1207 | 16S | m2G | 0.06695 | C >> A >> T~Del | 27 |
| U 1498 | 16S | m3U | 0.417 | G > A >> C~Del | 167 |
| C 1402 | 16S | m4Cm | 0.0118 | T > A~G No Del | 5 |
| A 1519 | 16S | m6,6 A | 0.168 | T > Del~G > C | 67 |
| A 1518 | 16S | m6,6 A | 0.0147 | T > G~Del > C | 6 |
| Background | 16S | | 0.0025 | | |

[a]RNA bases position on the ribosomal RNA.
[b]RNA molecule where the modification was observed.
[c]The type of modification as previously determined.
[d]Rate of mutation determined as explained in the materials and method part of this document.
[e]Substitution patterns determined from the alignments.
[f]The ratio of the frequency of mutation at a specific ribosomal RNA position over the average frequency of mutation on the whole RNA molecule

TABLE 2

All U positions containing a difference in mutation rate > 2%.

| Base[a] | RNA[b] | Modification[c] | CMC Mutation Rate[d] | Background Mutation Rate[e] | Differences in Mutation Rate[f] | Fold Change[g] |
|---|---|---|---|---|---|---|
| U 1921 | 23S | Ψ | 0.1274 | 0.0004 | 0.1270 | 319 |
| U 957 | 23S | Ψ | 0.1609 | 0.0011 | 0.1598 | 145 |
| U 2584 | 23S | Ψ | 0.2706 | 0.0027 | 0.2678 | 98 |
| U 2453 | 23S | D | 0.0590 | 0.0006 | 0.0584 | 98 |
| U 2609 | 23S | Ψ | 0.0595 | 0.0008 | 0.0588 | 77 |
| U 748 | 23S | Ψ | 0.0269 | 0.0004 | 0.0266 | 73 |
| U 2461 | 23S | Ψ | 0.0724 | 0.0011 | 0.0713 | 65 |
| U 2508 | 23S | Ψ | 0.0597 | 0.0010 | 0.0587 | 59 |
| U 1915 | 23S | Ψ | 0.0256 | 0.0008 | 0.0247 | 29 |
| U 2608 | 23S | Ψ | 0.0242 | 0.0011 | 0.0231 | 20 |
| U 1508 | 23S | None | 0.0528 | 0.0205 | 0.0323 | 2 |
| U 829 | 23S | None | 0.0464 | 0.0212 | 0.0252 | 1 |

[a]RNA bases position on the ribosomal RNA.
[b]RNA molecule where the modification was observed.
[c]The type of modification as previously determined.
[d]Rate of mutation determined as explained in the materials and method part of this document.
[e]Rate of mutation for the background sample as explained in the materials and method part of this document
[f]Differences in the rate of mutation of the CMCT treated sample and untreated background sample.
[g]The fold change in mutation rate caused by CMCT treatment, calculated as the ratio of the difference in mutation rates of the CMCT treated and untreated sample divided by the mutation frequency of the untreated sample.

TABLE 3

All G positions positions containing a difference in mutation rate > 2%.

| Base[a] | RNA[b] | Modification[c] | CMC Mutation Rate[d] | Background Mutation Rate[e] | Differences in Mutation Rates[f] | Fold Change[g] |
|---|---|---|---|---|---|---|
| G 2073 | 23S | m7G | 0.0795 | 0.0028 | 0.0767 | 27 |
| G 2894 | 23S | None | 0.0302 | 0.0076 | 0.0226 | 3 |

[a]RNA bases position on the ribosomal RNA.
[b]RNA molecule where the modification was observed.
[c]The type of modification as previously determined.
[d]Rate of mutation determined as explained in the materials and method part of this document.
[e]Rate of mutation for the background sample as explained in the materials and method part of this document
[f]Differences in the rate of mutation of the CMCT treated sample and untreated background sample.
[g]The fold change in mutation rate caused by CMCT treatment, calculated as the ratio of the difference in mutation rates of the CMCT treated and untreated sample divided by the mutation frequency of the untreated sample.

TABLE 4

All C positions containing a difference in mutation rate > 2%

| Base[a] | RNA[b] | Modification[c] | CMC Mutation Rate[d] | Background Mutation Rate[e] | Differences in Mutation Rates[f] | Fold Change[g] |
|---|---|---|---|---|---|---|
| C 2505 | 23S | OH5C | 0.1482 | 0.0130 | 0.1352 | 10 |
| C 1660 | 23S | None | 0.0889 | 0.0626 | 0.0263 | 0.4 |

[a]RNA bases position on the ribosomal RNA.
[b]RNA molecule where the modification was observed.
[c]The type of modification as previously determined.
[d]Rate of mutation determined as explained in the materials and method part of this document.
[e]Rate of mutation for the background sample as explained in the materials and method part of this document
[f]Differences in the rate of mutation of the CMCT treated sample and untreated background sample.
[g]The fold change in mutation rate caused by CMCT treatment, calculated as the ratio of the difference in mutation rates of the CMCT treated and untreated sample divided by the mutation frequency of the untreated sample.

[1] Zheng, G. Q., Dahl, J. A., Niu, Y. M., Fu, Y., Klungland, A., Yang, Y. G., and He, C. (2013) Sprouts of RNA epigenetics The discovery of mammalian RNA demethylases, *Rna Biology* 10, 915-918.

[2] Willyard, C. (2017) An epigenetics gold rush: new controls for gene expression, *Nature* 542, 406-408.

[3] McGuinness, D. H., and McGuinness, D. (2014) m6 a RNA Methylation: The Implications for Health and Disease, *Journal of Cancer Science and Clinical Oncology* 1, 1-7.

[4] Tang, C., Klukovich, R., Peng, H., Wang, Z., Yu, T., Zhang, Y., Zheng, H., Klungland, A., and Yan, W. (2017) ALKBH5-dependent m6A demethylation controls splicing and stability of long 3'-UTR mRNAs in male germ cells, *Proc Natl Acad Sci USA*.

[5] Desrosiers, R., Friderici, K., and Rottman, F. (1974) Identification of methylated nucleosides in messenger RNA from Novikoff hepatoma cells, *Proc Natl Acad Sci USA* 71, 3971-3975.

[6] Dominissini, D., Moshitch-Moshkovitz, S., Schwartz, S., Salmon-Divon, M., Ungar, L., Osenberg, S., Cesarkas, K., Jacob-Hirsch, J., Amariglio, N., Kupiec, M., Sorek, R., and Rechavi, G. (2012) Topology of the human and mouse m6A RNA methylomes revealed by m6A-seq, *Nature* 485, 201-206.

[7] Bodi, Z., Button, J. D., Grierson, D., and Fray, R. G. (2010) Yeast targets for mRNA methylation, *Nucleic Acids Res* 38, 5327-5335.

[8] Liu, N., Parisien, M., Dai, Q., Zheng, G., He, C., and Pan, T. (2013) Probing N6-methyladenosine RNA modification status at single nucleotide resolution in mRNA and long noncoding RNA, *RNA* 19, 1848-1856.

[9] Gentry, R. C., Childs, J. J., Gevorkyan, J., Gerasimova, Y. V., and Koculi, E. (2016) Time course of large ribosomal subunit assembly in *E. coli* cells overexpressing a helicase inactive DbpA protein, *RNA* 22, 1055-1064.

[10] Schwartz, S., Bernstein, D. A., Mumbach, M. R., Jovanovic, M., Herbst, R. H., Leon-Ricardo, B. X., Engreitz, J. M., Guttman, M., Satija, R., Lander, E. S., Fink, G., and Regev, A. (2014) Transcriptome-wide mapping reveals widespread dynamic-regulated pseudouridylation of ncRNA and mRNA, *Cell* 159, 148-162.

[11] Bakin, A. V., and Ofengand, J. (1998) Mapping of pseudouridine residues in RNA to nucleotide resolution, *Methods Mol Biol* 77, 297-309.

[12] Lovejoy, A. F., Riordan, D. P., and Brown, P. O. (2014) Transcriptome-wide mapping of pseudouridines: pseudouridine synthases modify specific mRNAs in *S. cerevisiae*, *PLoS One* 9, e110799.

[13] Xing, F., Hiley, S. L., Hughes, T. R., and Phizicky, E. M. (2004) The specificities of four yeast dihydrouridine synthases for cytoplasmic tRNAs, *J Biol Chem* 279, 17850-17860.

[14] Behm-Ansmant, I., Helm, M., and Motorin, Y. (2011) Use of specific chemical reagents for detection of modified nucleotides in RNA, *J Nucleic Acids* 2011, 408053.

[15] Maden, B. E. (2001) Mapping 2'-O-methyl groups in ribosomal RNA, *Methods* 25, 374-382.

[16] Incarnato, D., Anselmi, F., Morandi, E., Neri, F., Maldotti, M., Rapelli, S., Parlato, C., Basile, G., and Oliviero, S. (2017) High-throughput single-base resolution mapping of RNA 2-O-methylated residues, *Nucleic Acids Res* 45, 1433-1441.

[17] Homan, P. J., Favorov, O. V., Lavender, C. A., Kursun, O., Ge, X., Busan, S., Dokholyan, N. V., and Weeks, K. M. (2014) Single-molecule correlated chemical probing of RNA, *Proc Natl Acad Sci USA* 111, 13858-13863.

[18] Krokhotin, A., Mustoe, A. M., Weeks, K. M., and Dokholyan, N. V. (2017) Direct identification of base-paired RNA nucleotides by correlated chemical probing, *RNA* 23, 6-13.

[19] Siibak, T., and Remme, J. (2010) Subribosomal particle analysis reveals the stages of bacterial ribosome assembly at which rRNA nucleotides are modified, *RNA* 16, 2023-2032.

[20] Siegfried, N. A., Busan, S., Rice, G. M., Nelson, J. A., and Weeks, K. M. (2014) RNA motif discovery by SHAPE and mutational profiling (SHAPE-MaP), *Nat Methods* 11, 959-965.

[21] Smola, M. J., Rice, G. M., Busan, S., Siegfried, N. A., and Weeks, K. M. (2015) Selective 2'-hydroxyl acylation analyzed by primer extension and mutational profiling (SHAPE-MaP) for direct, versatile and accurate RNA structure analysis, *Nat Protoc* 10, 1643-1669.

[22] Shajani, Z., Sykes, M. T., and Williamson, J. R. (2011) Assembly of bacterial ribosomes, *Annu Rev Biochem* 80, 501-526.

[23] Busan, S., and Weeks, K. M. (2017) Accurate detection of chemical modifications in RNA by mutational profiling (MaP) with ShapeMapper 2, *RNA*.

It should be borne in mind that all patents, patent applications, patent publications, technical publications, scientific publications, and other references referenced herein and in the accompanying appendices are hereby incorporated by reference in this application to the extent not inconsistent with the teachings herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

What is claimed is:

1. A method for detecting a naturally occurring RNA post-transcriptional modification in a sample, comprising:
performing a reverse transcription reaction of an RNA in the presence of $Mn^{2+}$ to generate cDNA, wherein the $Mn^{2+}$ is at a concentration sufficient to induce a base misincorporation at a location of the RNA comprising a nucleoside modification; and
performing next generation sequencing on the cDNA under conditions to detect the base misincorporation, and
determining, based on the base misincorporation, one or more nucleoside modifications comprising m2G (N2-methylguanosine), m3Ψ (3-methylpseudouridine), 5-hydroxylC (5-hydroxyl cytosine), m7G (7-methylguanosine), m4Cm (N4,2'-O-dimethylcytosine), m3U (3-methyluridine), m6,6 A (N6, N6-dimethyladenosine), m1G (1-methylguanosine), m6 A (N6-methyladenosine), Cm (2'-O-methylcytidine), Um (2'-O-methyluridine), Am (2'O-methyladenosine), Gm (2'-O-methylguanosine), Ψ (pseudouridine), dihydrouridine (D) or a combination thereof; and, optionally, determining, based on the base misincorporation m1A (1-methyladenosine).

2. The method of claim 1, wherein the nucleoside modification comprises m2G (N2-methylguanosine), m3Ψ (3-methylpseudouridine), 5-hydroxylC (5-hydroxyl cytosine), m7G (7-methylguanosine), m4Cm (N4,2'-O-dimethylcytosine), m3U (3-methyluridine), m6,6 A (N6, N6-dimethyladenosine), m1G (1-methylguanosine), dihydrouridine (D) or a combination thereof.

3. The method of claim 1, wherein the nucleoside modification comprises m6 A (N6-methyladenosine), m5U (5-methyluridine), Cm (2'-O-methylcytidine), Um (2'-O-methyluridine), Am (2'O-methyladenosine), Gm (2'-O-methylguanosine), Ψ (pseudouridine), m1A (1-methyladenosine), or a combination thereof.

4. The method of claim 1, wherein performing the next generation sequencing comprises
Converting the cDNA fragments into dsDNA;
Fragmenting the dsDNA; and
Performing sequencing on the dsDNA fragments that employs pyrosequencing, sequencing by ligation or sequencing by synthesis methodologies.

5. A method for detecting an RNA post-transcriptional modification in a sample, comprising
identifying one or more mutations in a DNA nucleic acid sequence in the sample made as a result of subjecting a RNA to reverse transcriptase in the presence of Mn2+; wherein a locus of a mutation of the one or more mutations represents a nucleoside modification.

6. The method of claim 5, wherein the sample comprises a dsDNA library of fragments and further comprising performing next generation sequencing on the dsDNA library of fragments.

7. The method of claim 6, wherein performing next generation sequencing on the dsDNA library of fragments comprises obtaining sequence data via pyrosequencing, sequencing by ligation or sequencing by synthesis methodologies; and aligning the sequence data to generate aligned sequence data.

8. The method of claim 7 further comprising comparing the aligned sequence data to a reference sequence and calculating mutation frequencies in the aligned sequence data.

9. The method of claim 5, further comprising identifying nucleoside modification type of the nucleoside modification based on a substitution pattern of the corresponding mutation.

10. The method of claim 1, wherein the one or more nucleoside modifications are selected from m4 Cm, m6, 6A, pseudouridine, M3pseudouridine, m7G, OH5C and D.

11. The method of claim 1, further comprising, before the performing step, subjecting the RNA to alkaline treatment, optionally following N-cyclohexyl-N-β(4-methylmorpholinium) ethylcarbodiimide p-tosylate (CMCT) treatment.

* * * * *